United States Patent [19]

Kitajima et al.

[11] Patent Number: 5,876,605
[45] Date of Patent: Mar. 2, 1999

[54] PREPARATION OF PLASMA OR SERUM SAMPLE FROM WHOLE BLOOD

[75] Inventors: Masao Kitajima; Kenichiro Yazawa, both of Saitama, Japan

[73] Assignee: Fuji Photo Film Co., Ltd., Kanagawa, Japan

[21] Appl. No.: 784,480

[22] Filed: Jan. 17, 1997

[30] Foreign Application Priority Data

Jan. 19, 1996 [JP] Japan .................................. 8-007691

[51] Int. Cl.$^6$ ................................................. B01D 61/00
[52] U.S. Cl. ........................ 210/650; 210/645; 210/651; 210/653; 210/654; 210/723; 210/767; 435/2; 436/177; 436/178
[58] Field of Search ..................... 210/645, 650, 210/651, 653, 654, 767, 749, 723, 724, 725, 753, 488, 489, 490, 496, 500.41, 503, 505, 506, 507, 508; 436/175, 177, 178; 435/2

[56] References Cited

U.S. PATENT DOCUMENTS

| | | |
|---|---|---|
| 3,552,925 | 1/1971 | Fetter . |
| 3,552,928 | 1/1971 | Fetter . |
| 4,678,566 | 7/1987 | Watanabe et al. ....................... 210/143 |
| 5,118,428 | 6/1992 | Sand et al. .............................. 210/749 |
| 5,208,142 | 5/1993 | Genshaw ................................. 436/175 |
| 5,423,989 | 6/1995 | Allen et al. ............................. 210/650 |

OTHER PUBLICATIONS

Database WPI–Derwent Publications AN 92–303877 & JP 04 208 856 A–Sanwa Kagaku Kenkyusho Co.
Database WPI–Derwent Publications AN 90–295055 & JP 04 208 565 A–Fuji Photo Film Co. Ltd.

Infusionstherapie 19, 1992, pp. 187–189, Coden–1FTRE3, XP000671432–Taborshi, et al.–"Application of an Automated Plasma Filtration Device and a Blood Monitoring system for LDL Apheresis".

Vos Sang (1976), 31,4, pp. 289–295 Coden, Vosaad–XP000671437–Friedli, et al–"Studies on New Process Procedures in Plasma Fractionation on an Industrial Scale", III Removal of Precipitates by Filtration through a Horizontal Leaf Filter with Centrifugal Cleaning (Funda Filter) as an Alternative to Tubular–Bowl Centrifuges.

*Primary Examiner*—John Kim
*Attorney, Agent, or Firm*—McAulay Nissen Goldberg Kiel & Hand, LLP

[57] ABSTRACT

The method of the invention is for preparing a plasma or serum sample from whole blood and includes mixing an aqueous solution of an inorganic salt or an amino acid or salt thereof with the whole blood in an amount of 20% or less of the whole blood volume so that concentration of the inorganic salt or the amino acid or salt thereof becomes 10 to 200 $\mu$mol/1 ml whole blood, and then, filtering the whole blood to remove blood cell components. According to the method of the invention, plasma separation from whole blood can be achieved efficiently, and recovered volume of plasma can be increased. By selecting reagent, good plasma which has no deviation in component viewpoint, and which is possible to measure in the same level accuracy as a plasma obtained by centurifuging, can be obtained through a simple filtration operation.

6 Claims, 2 Drawing Sheets

PREPARATION OF PLASMA OR SERUM SAMPLE FROM WHOLE BLOOD

BACKGROUND OF THE INVENTION

This intention relates to a method of preparing a plasma or serum sample from whole blood, especially to a method capable of obtaining a plasma or serum sample from whole blood having a high hematocrit value in a high separation rate without destroying blood cells.

Type or concentration of blood components, such as metabolites, proteins, lipids, electrolytes, enzymes, antigens, and antibodies, is measured, in general, using a plasma or serum sample obtained by centrifuging whole blood. However, centrifuging takes labor and time. Particularly, centrifuging is unsuitable for an urgent case of measuring a small number of samples promptly and in site inspection, because of requiring a centrifuge and electricity. Thereupon, it has been investigated to separate serum from whole blood by filtration.

Several filtration methods using glass fiber filter have been known wherein whole blood is charged into the glass fiber put in a column from one side of the column, and plasma or serum is obtained from the other side (Japanese Patent KOKOKU Nos. 44-14673, 5-52463, Japanese Patent KOKAI Nos. 2-208565, 4-208856)However, practical filtration methods capable of obtaining an amount of plasma or serum necessary for measuring by an automatic analyzer from whole blood have not been developed except a part of items, such as blood sugar.

The reason is seemed that previous filtration systems do not satisfy the following three conditions 1) It is difficult to obtain a sufficient amount of plasma necessary for automatic analysis by filtration.

2) Erythrocytes tend to destroy (hemolyze) through filtration, and accordingly, it is difficult to measure analytical items which are liable to be affected by hemoglobins released into plasma or serum by hemolysis or analytical items wherein quantity in blood cells is greater than plasma or serum, such as GOT, GPT, LDH, Va and K.

3) In the case of high hematocrit value (50% or more) samples, it is difficult to filter because of clogging filtering material by erythrocytes.

For example, Japanese Patent KOKOKU No. 6-64054 discloses plasma filtration technique by glass fiber filter made of a particular material, but it states that plasma amount capable of taking out shall be limited to ½ or less of the volume of glass fiber filter. In the Japanese patent, on the premise that hematocrit value is 50%, it is supposed that space of glass fiber filter is filled out by erythrocytes, and the quantity of plasma obtained by filtering up to the filled out state is set 50% of the volume of glass fiber filter at maximum However, whole blood samples having a hematocrit value of 55 to 60% are not rare among whole blood samples daily dealt in clinical assay organization.

SUMMARY OF THE INVENTION

An object of the invention is to provide a sure means capable of separating plasma or serum by filtration even from high hematocrit value whole blood samples having a hematocrit value of 60 to 70% which are a great obstacle upon separating plasmas from whole bloods, actually recorded among newborns and patients suffering from dehydration.

Another object of the invention is to provide a sure means capable of separating plasma or serum in an amount of 100 $\mu$l or more, which is necessary for the measurement of plural items by a usual automatic analyzer for clinical assay, from a sample having any hematocrit value without limiting the recovering amount of plasma to ½ of glass fiber filter volume.

Still another object of the invention is to provide a means capable of obtaining plasma with good quality without destruction of blood cell components which is suitable for the measurement of most assay items among clinical chemical assay and immunoserum assay, which is difficult to realize by conventional filtration using a column.

Problems in development of plasma-separating technique from whole blood are summarized in the following three points, (1) Not to destroy erythrocytes (hemolyze) in plasma separation When erythrocytes are destroyed, blood cell components of which quantity in blood cells is much greater than in plasma, such as Hb, GOT, LDH and K are released into plasma to cause analytical error. Hb released into plasma interferes with optical measurement.

(2) Sure plasma separation even from whole bloods having a high hematocrit value (50% or more) with difficulty in erythrocyte separation, and having tendency to hemolysis. When hematocrit value rises, separation by filtration becomes difficult due to sharp increase of blood viscosity.

(3) Variation of composition do not occur in plasma separation.

The inventors investigated in order to solve the above problems and to develop a means capable of separating plasma in a high separation rate without hemolysis even from a high hematocrit value whole blood, and have achieved the objects by adding an agent capable of lowering hematocrit value to whole blood in a particular concentration, and then separating plasma.

Thus, the present invention provides a method of preparing a plasma or serum sample from whole blood which comprises mixing an aqueous solution of an inorganic salt or an amino acid or salt thereof with the whole blood in an amount of 20% or less of the whole blood volume so that concertration of said inorganic salt or said amino acid or salt thereof becomes 10 to 200 $\mu$mol/1 ml whole blood, and then, filtering the whole blood to remove blood cell components.

1 Filter unit
2 Filter holder
3 Syringe
4 Holder body
5 Cap
6 Filter chamber
7 Sample intake
8 Nozzle
9 Suction part
10 Glass fiber filter sheet
11 Cellulose filter sheet
12 Double face adhesive tape
13 Polysulfone microporous membrane
14 Flow area-regulating member

DETAILED DESCRIPTION OF THE INVENTION

The whole blood sample to which the method of the invention is applicable may contain various anticoagulant or glycolysis inhibitor, such as heparin, NaF, EDTA or monoiodoacetate, or not. The method of the invention is effective especially against high hematocrit bloods, e.g. having a hematocrit (Hct) value of 50 to 70%, particularly 55 to 70%.

The inorganic salt and amino acid and salt thereof are an agent (HL agent) having an action to accelerate separation between blood cells and plasma to decrease hematocrit value.

The HL agent which is the inorganic salt, amino acid or salt thereof is water-soluble and has a solubility of 100 mmol/l or more, preferably 1 mol/l or more, particularly 3 mol/l or more. Exemplary inorganic salts are combinations of monovalent or divalent alkals metal or alkaline earth metal and halogen, $NO_3$, $SO_4$, or $CO_3$, such as NaCl, $CsCl_2$, $Li_2SO_4$, $CaCl_2$, $Rb_2SO_4$ and $Cs_2SO_4$. Exemplary amino acids are natural amino acids, such as Gly, Ala, Asp, Glu and glycinamide asparagine. The inorganic salt, amino acid and salt thereof are made so that pH of their aqueous solution is 5 to 8, preferably 6 to 7.5, and therefore, the inorganic salt and amino acid salt may be a hydrogen salt, such as $NaHCO_3$. Acidic amino acids, such as Asp and Glu, may be made into a salt of alkali metal or alkaline earth metal or the like, and basic amino acids, such as Lys and Arg, may be made into a salt of halogen, $NO_3$, $SO_4$, $CO_3$ or the like.

The HL agent be used is selected by considering subject matter to be measured, i.e. a component to be measured. For example, when sodium or chloride in blood is measured, NaCl is unsuitable as the HL agent. Phosphate is unsuitable as the HL agent for measuring inorganic phosphorus in blood, Moreover, HL agent which influences reactivity of reagents used for measurement cannot be used.

For example, HL agent containing magnesium, iron, copper, barium, zinc, or the like cannot be used for measuring calcium, because they interfere with calcium measurement.

The HL agent is used as an aqueous solution, A suitable concentration of the HL agent is 0.1 to 5 mol/l, preferably 0.5 to 3 mol/l, more preferably 1 to 2.5 mol/l.

Other components may be added to the aqueous HL agent solution. For example, glycerine, ethylene glycol, polyethylene glycol or the like may be added for the purpose of prevention against drying. A buffer may be added for the purpose of pH adjustment. Furthermore, according to the object of analysis, various compounds may be added in order to facilitate separation of analyte in filtered plasma. Exemplary of the compounds are selective binding reagents for LDL chorestherol, such as dextrin and tungstophosphoric acid, which are fractionation agent for the measurement of HDL chorestherol. Other exemplary compounds are having reactivity with a particular component in plasma, such as various antigens and antibodies including modified ones.

By adding the HL agent, flexibility of erythrocyte membrane decreases, and erythrocytes become resistant to deformation. It is known that erythrocyte passes through a considerably smaller space, e.g. a capillary 1–2 $\mu$m in diameter, than apparent size of erythrocyte during filtering whole blood. However, by adding the HL agent, since deformation of erythrocytes is restrained, filtration can be conducted very smoothly.

Reduction of hematocrit value by the HL agent is in proportion to molar concentration of the HL agent in plasma volume of whole blood to which the HL agent is added. On the other hand, in a HL agent concentration of more than 200 mmol/l, destruction of blood cells (hemolysis) tends to occur, and hemoglobin which is the main component of erythrocyte elutes into plasma. Accordingly, a suitable amount of the HL agent added to whole blood is 10 to 200 $\mu$mol, preferably 10 to 100 $\mu$mol, more preferably 20 to 60 $\mu$mol, per 1 ml whole blood. Volume of aqueous HL agent solution to be added is not especially limited. However, too large volume is undesirable, because the dilution rate of whole blood is great resulting in the degradation of accuracy in weighing. Moreover, when dilution rate is high, measuring accuracy is a problem in relation measuring sensitivity. Thereupon, a suitable volume of the aqueous HL agent solution to be added is 20% or less, preferably 10% or less, more preferably 5% or less of whole blood by volume ratio. The lower limit of the volume of the aqueous HL agent solution depends on the water-solubility of HL agent, etc., and in general, 1% or more. In the method of the invention, filtering ability is improved by adding only a small amount of HL agent, influence on measuring sensitivity and accuracy is small.

When HL agent is added to whole blood., the HL agent is dissolved into plasma to elevate osmotic pressure of plasma to generate osmotic pressure difference between plasma and the inside of blood cells. Then, force acts so as to loosen the difference of osmotic pressure. That is, water in blood cell is discharged into plasma to elevate osmotic pressure (i.e. concentration of solute) in blood cells and to lower osmotic pressure of plasma. As a result, volume of blood cell decreases and volume of plasma increases, resulting in the decrease of hematocrit value. By adding HL agent, volume of erythrocyte decreases and flexibility of blood cell membrane decreases, and accordingly, filtration using a filtering material, such as porous membrane is facilitated.

Moreover, since quantity of free plasma increases, recovery rate of plasma by filtration is improved.

Although the lowering of hematocrit value caused by HL agent increases together with the increase of HL agent concentration, since strength of blood cell membrane is weak, blood cell is liable to destroy and hemolyze at high HL agent concentration. Since the action of HL agent is mainly derived from its osmotic pressure, the action is proportional to the number of solute molecules in whole blood (exactly in plasma). When the added amount of HL agent is too great, osmotic pressure difference between the inside and outside of blood cell becomes too great. As a result, blood cell is ruptured or blood cell membrane is punctured to leak components in blood cell into plasma.

In general, blood assay is based on the measurement of concentration of plasma component. When erythrocytes are destroyed or blood cell membranes are purctured, components in erythrocytes are leaked into plasma portion, Since erythrocyte contains Hb (hemoglobin) in a high concentration, when leakage occurs, plasma becomes red (called hemolysis) Even if the destruction of erythrocytes is very small, coloring of plasma caused by the leakage of Hb cannot be ignored, and in some analytical items, the leakage strongly influences analytical value. For example, in a blood assay of healthy persons, when 0.1% of total blood cells are destroyed, measured values of most enzymes, such as CPK and ALP, are not accurate, Some components (GOT, GPT, LDH, K) exist in erythrocyte in a higher concentration than plasma, and the measurement of those components is directly influenced by hemolysis. Accordingly, it is necessary to conduct separation, recovery of plasma under conditions where hemolysis occurs as small as possible.

Whole blood of healthy person contains usually about 15 g/dl hemoglobin (Hb). Influence by leaked hemoglobin is different according to measuring method and measuring item.

For example, influence of hemolysis upon measurement of blood sugar and choresterol is small, and even when about 150 mg/dl hemoglobin exists in plasma (corresponding to hemolysis of 1% of total erythrocytes), they are measured accurately.

On the other hand, GOT, GPT, LDH, K and the like are liable to be influenced by hemolysis, and particularly, in the case of LDH or K, even when hemoglobin concentration is 15 mg/dl (corresponding to hemolysis of 0.1% of total erythrocytes), measured values are influenced significantly in view of clinical diagnosis.

Accordingly, in the case of measuring blood sugar and choresterol alone, plasma separation may be incomplete. However, in the case of measuring GOT, GPT, LDH, K, etc., hemolysis must be less than 0.1%.

Hematocrit value of healthy persons is 40 to 45%, but whole blood samples having a hematocrit value of 55 to 60% are dealt at a frequency of several percents in daily clinical assay. In such high Hct samples, Hb content is 20 to 25 g/dl. If allowance of measurement against Hb is 15 mg/dl, hemolysis of high Hct samples must be restrained to less than 0.07%.

When inorganic salt, amino acid or salt thereof or agglutinin such as lectin is dissolved directly in blood from a dry state or from impregnated into filter paper or porous material, followed by drying, blood contacts the dry matter. Blood is liable to hemolyze locally and temporarily in a initial stage of dissolving the dry matter in plasma. Accordingly, plasma obtained through the above process frequently contains hemoglobin which is not so much. The plasma has no problem for measuring blood sugar or choresterol, but has a problem for measuring GOT, GPT, LDH, K and the like. The tendency is more remarkable in high HcT samples.

On the other hand, when the above compound is dissolved in water to make an aqueous solution with a suitable concentration, the degree of local concentration elevation is small upon mixing the aqueous solution into plasma proceeds smoothly. As a result, hemolysis only rarely occurs.

An amount of blood to be used is about 0.3 to 3 ml, usually about 0.5 to 1.5 ml, and mixing of aqueous HL agent solution with whole blood may be carried out only by several times shaking. It is supposed that the action of HL agent is in a moment, and the mixture reaches equilibrium within several seconds. Accordingly, it is not necessary to adjust temperature or time upon mixing.

After mixing HL agent solution with whole blood sample, the whole blood sample is filtered. As the filtering material, various known filtering material capable of separating blood cells can be used. Illustrative of the filtering materials are glass fiber filter, microporous membranes haying blood cell-separating ability such as made of fluorine-containing polymer, of which the surface has been made hydrophilic, or polysulfone, laminates of glass fiber filter and microporous membrane, laminates of glass fiber filter and cellulose filter, laminates of glass fiber filter, cellulose filter and microporous membrane, laminates of fibrous porous membrane and non-fibrous porous membrane disclosed in Japanese Patent KOKAI Nos. 62-138756-8, 2-105043, 3-16651, etc. Preferred ones are containing glass fiber filter, and laminates of glass fiber filter and microporous membrane, laminates of glass fiber filter and cellulose filter, and laminates of glass fiber filter, cellulose filter and microporous membrane are particularly preferred. Filter materials containing polysulfone microporous membrane are also preferable. The most preferable ones are laminates of glass fiber filter, cellulose filter and microporous membrane, especially using polysulfone membrane as the microporous membrane.

Preferable glass fiber filter has a density of about 0.02 to 0.3 g/cm$^3$ preferably about 0.05 to 0.2 g/cm$^3$, more preferably about 0.07 to 0.15 g/cm$^3$, a retainable particle size of about 0.8 to 9 $\mu$m, preferably 1 to 5 $\mu$m. By treating the surface of glass fiber with hydrophilic polymer as disclosed in Japanese Patent KOKAI Nos. 2-208565, 4-208856, filtration can be conducted more fast and smoothly. The surface of glass fiber may be treated with lectin. Two or more glass fiber filters may be lamirated.

Microporous membranes having blood cell-separating ability of which the surface has been made hydrophilic separate whole blood specifically into blood cells and plasma without hemolysis to the degree of substantially influencing analytical values. A suitable pore size of the microporous membrane is smaller than the retainable particle size of glass fiber filter, and is 0.2 $\mu$m or more, preferably about 0.3 to 5 $\mu$m, more preferably about 0.5 to 4.5 $\mu$m, particularly preferably about 1 to 3 $\mu$m. The void content of the microporous membrane is preferably higher, and a suitable void content is about 40 to 95%, preferably about 50 to 95%, more preferably about 70 to 95%. Illustrative of the microporous membranes are polysulfone membrane, fluorine-containing polymer membrane, cellulose acetate membrane, nitrocellalose membrane, etc. The surface of the membrane may be hydrolyzed or may be rendered hydrophilic by a hydrophilic polymer or an activating agent.

As the fluorine-containing polymer membranes, there are the microporous matrix membrane (microporous layer) composed of polytetrafluoroethylene fibrils (fines) disclosed in WO 87/02267, Gore-Tex (W. L. Gore and Associates), Zitex (Norton), Poreflon (Sumitomo Denki), etc. Other fluorine-containing polymer sheets usable as the microporous layer include polytetrafluoroethylene microporous membranes disclosed in U.S. Pat. No. 3,368, 872 (Examples 3 and 4), U.S. Pat. No. 3,260,413 (Examples 3 and 4), U.S. Pat. No. 4,201,548, etc., polyvinylidenefluoride microporous membranes disclosed in U.S. Pat. No. 3,649,505 and the like, The microporous membrane of fluorine-containing polymer may be prepared by using a single fluorine-containing polymer or blending two or more kinds of fluorine-containing polymers of further blending one or more polymers not containing fluorine or fibers therewith. As the structure, there are unstretched one, uniaxially stretched one, biaxially stretched one, nonlaminated single layer type, laminated double layer type, such as a membrane laminated to another membrane structure such as a fiber membrane In the case of nonlaminated type microporous membrane having fibril structure or having been uniaxially or biaxially stretched, microporous membrane having a great void content and a short filtering pass can be prepared by stretching. In microporous membranes having a short filtering pass, clogging rarely occurs by solid components (mainly red blood cells) in blood, and the separation time of blood cells and plasma is short. As a result, accuracy in quantitative analysis is improved, The adhesive strength of adhesive used for the partial adhesion to the adjacent microporous membrane can be strengthened by providing the physical activation (preferably glow discharge or corona discharge) disclosed in U.S. Pat. No. 4,783,315 on at least one side of the microporous membrane of fluorine-containing polymer to render hydrophilic.

It is wellknown that fluorine-containing polymer microporous membranes as it is have a low surface tension. As a result, when the membrane is used as the blood cell filtering layer, aqueous liquid samples are repelled and do not diffuse nor permeate over the surface or into the inside.

In the invention, the above repelling problem has been resolved by incorporating a sufficient amount of surfactant for rendering the outer surface and the inner space surface of the fluorine-containing polymer microporous membrane substantially hydrophilic thereinto. In order to impart a hydrophilic property sufficient for diffusing, permeating or moving an aqueous liquid sample over the surface or into the inside of the fluorine-containing polymer microporous membrane without repelling to the membrane, in general, it is necessary that the space surface of the membrane is coated with a surfactant in an amount of about 0.01 to 10%, preferably about 0.1 to 5%, more preferably about 0.1 to 1% of the void volume of the membrane, For example, in the case of a fluorine-containing polymer microporous membrane 50 $\mu$m in thickness, a preferred amount of surfactant to be impregnated is usually in the range of 0.05 to 2.5 g/m$^2$. As the method of impregnating surfactant into a fluorine-containing microporous membrane, a common method cmoprises immersing the fluorine-containing microporous membrane in the surfactant solution dissolved in a low boiling point (a preferable boiling point is in the range of about 50° C. to about 12° C.) organic solvent (e.g. alcohols, esters, ketones) to permeate into the inner spaces of the membrane substantially sufficiently, taking the membrane out of the solution slowly, and then drying by blowing air (preferably warm air).

As the surfactant for rendering the fluorine-containing polymer microporous membrane hydrophilic, the surfacetant may be nonionic, anionic, cationic or ampholytic. However, nonionic surfactants are advantageous for the multilayer analytical elements for analyzing whole blood samples, because nonionic surfactants have a relatively low hemolytic activity among the above surfactants, Suitable nonionic surfactants include alkylphenoxypolyethoxyethanol, alkylpolyether alcohol, polyethyleneglycol monoester, polyethyleneglycol diester, higher alcohol-ethylene oxide adduct (condensate), polyol ester-ethylene oxide adduct (condensate), higher fatty acid alkanol amide, etc. Examples of the nonionic surfactant are as follows: As the alkylphenoxypolyethoxyethanol, there are isooctylphenoxypol y-ethoxyethanols (Triton X-100; containing 9–10 hydroxyethylene units on average, Triton X-45; containing 5 hydroxyethylene units on average) and nonylphenoxypolyethoxyethanols (IGEPAL CO-630; containing 9 hydroxyethylene units on average, IGEPAL CO-710; containing 10–11 hydroxyethylene units on average, LENEX 698; containing 9 hydroxyethylene units, on average). As the alkylpolyether alcohol, there are higher alcohol polyoxyethylene ethers (Triton X-67; CA Registry No. 59030-15-8), etc.

The fluorine-containing polymer microporous membrane may be rendered hydrophilic by providing one or more water-insolubilized water-soluble polymers in its porous spaces. The water-soluble polymers include oxygen-containing hydrocarbons, such as polyacrylamide, polyvinylpyrrolidone, polyvinylamine and polyethyleneimine, negative charge-containing ones such as polyvinyl alcohol, polyethylene oxide, polyethylene glycol, methyl cellulose, ethyl cellulose, hydroxyethyl cellulose and hydroxypropyl cellulose, nitrogen-containing ones, such as polyacrylic acid, polymetacrylic acid and polystyrene sulfonic acid, and the like. The water-insolubilization may be conducted by heat treatment, acetal-inducing treatment, esterification, chemical reaction by potassium dichromate, crosslinking by ionizable radiation, or the like. Details are disclosed in Japanese Patent KOKOKU Nos. 56-2094 and 56-16187.

The polysulfone microporous membrane can be prepared by dissolving polysulfone into dioxane, tetrahydrofuran, dimethylformamide, dimethylacetamide, N-methyl-2-pyrolidone or a mixed solvent thereof to obtain a raw liquid for forming film, casting into film by flowing directly into a coagulating solution, washing, and then drying. Details are disclosed in Japanese Patent KOKAI No. 62-27006. In addition, polysulfone microporous membranes are also disclosed in Japanese Patent KOKAI Nos. 56-12640, 56-86941, 56-154051, etc., and they are applicable to the invention. The polysulfone microporous membrane can be rendered hydrophilic, similar to the fluorine-containing polymer, by incorporating surfactant or providing water-insolubilized water-soluble polymer.

Preferable nonfibrous porous membranes, in the laminate of a fibrous porous membrane and a nonfibrous porous membrane are blushed polymer membranes composed of a cellulose ester, such as cellulose acetate, cellulose acetate/butyrate or cellulose nitrate, disclosed in U.S. Pat. No. 3,992.158 or U.S. Pat. No. 1,421,341. The nonfibrous porous membrane may be a microporous membrane of polyamide, such as 6-nylon or 6,6-nylon, or polyethylene, polypropylene, or the like. Other nonfibrous porous membranes usable for the blood cell-separating filter include continuous microspace-containing porous membranes where polymer particulates, glass particulates, diatomaceous earth or the like are joined by a hydrophilic or non-water-adsorptive polymer, such as disclosed in U.S. Pat. No. 3,992,158, and U.S. 4,258,001.

Preferable effective pore size of the nonfibrous porous membrane is 0.2 to 10 $\mu$m, preferably 0.3 to 5 $\mu$m, particularly preferably 0.5 to 5 $\mu$m. The effective pore size of the nonfibrous porous membrane in the invention is the pore size measured by the bubble point method according to ASTM F316-70. In the case that the nonfibrous porous membrane in a membrane filter composed of blushed polymer prepared by the phase separation method, the liquid passages in the thickness direction are, in general, the narrowest at the free surface (glossy face) in the manufacturing process of the membrane, and the pore size in section of each liquid passage stipulated a circle is the smallest near the free surface The minimum pore size of passages in the thickness direction per unit area has a distribution in facial direction of the membrane filter, and the maximum value determines filtration performance In general, it is determined by the limit bubble point method.

As mentioned above, in the membrane filter composed of blushed polymer prepared by the phase separation method, liquid passages in the thickness direction become the narrowest at the free surface (glossy face) in the manufacturing process of the membrane. In the case of using the membrane as the nonfibrous porous membrane of the filtering material of the invention, it is preferable to face the glossy face of the membrane filter toward the side to discharge the plasma portion.

The material composing the fibrous porous membrane may be filter paper, nonwoven fabric, woven fabric such as plain weave fabric, knitted fabric such as tricot fabric, etc. Among them, woven fabric and knitted fabric are preferred. The woven fabric or the like may be treated by blow discharge as disclosed in Japanese Patent KOKAI No. 57-66359.

The void volume (per unit area) of the fibrous porous membrane may be equal to or different from the nonfibrous porous layer. The void volume correlation between them may be adjusted by changing either or both of void content and thickness.

In the case that the filtering material used in the invention is a laminate, respective layers may be integrated by joining each other using partially disposed (e.g. spots) adhesive, according to disclosures in Japanese Patent KOKAI Nos. 62-138756-8, 2-105043, 3-16651, etc.

In the filtering material of the invention, it is thought that the filter material does not trap blood cells only by the surface, but catches to remove blood cells gradually by entangling at first large blood cell components and then smaller blood cell components in the space structure with permeating in the thickness direction in total of the filtering material called the volumetric filtration.

In the system of the invention, density, thickness, area, etc. of the filtering material may be arranged according to the supplied, i.e. to be separated, volume of blood. In the case of using glass fiber filter, a volume of plasma or serum to be recovered becomes so as to be 10% or more, preferably 20 to 100%, particularly preferably 30 to 70% of the volume of the glass fiber filter. Actually, it is preferably to use a glass fiber filter having a volume about twice as much as the volume of plasma to be recovered.

A supply volume of whole blood to be filtered is not restricted. Although the volume of whole blood is smaller than the volume of glass fiber filter, plasma can be separated. However, the ratio (recovery) of recovered volume of plasma to the volume of whole blood is small In the case that the volume of whole blood is greater than the volume of glass fiber filter, space of the glass fiber filter is filled out by blood cells, and then, leakage of blood cells occurs from glass fiber filter. If a microporous membrane is provided, leaked blood cells are caught by the microporous membrane. As a result, volume of recovered plasma increases compared with using glass fiber filter alone. In general, a suitable volume ratio of whole blood:glass fiber filter is 0.5 to 10:1, preferably 0.7 to 5:1, more preferably 0.8 to 3:1.

Upon filtering, it is preferable to accelerate filtration by pressurizing from blood supply side of sucking from the opposite side. A preferable volume (e.g. sectional area of priston×stroke in syringe) for inducing the pressurizing or sucking conditions is twice to 5 times as large as the volume of filtering material. The pressurizing or sucking period is not strictly restricted. However, in order to prevent homolysis, the period is within 60 seconds wherein filtration is preferably accomplished rapidly. For example, in the case of filtering 1 ml whole blood, a suitable pressurizing or sucking period is 1 to 60 seconds, preferably 2 to 30 seconds, more preferably 5 to 20 seconds, and thereafter, pressure is returned to atmospheric pressure promptly.

As mentioned above, in the system of the invention, plasma volume to be recovered is previously set, and glass fiber filter volume corresponding thereto was set. Then, a sufficient volume of blood is supplied, and pressurized or sucked. When a prescribed volume of plasma is obtained or a prescribed period is over, pressure is returned to atmospheric pressure. Plasma or serum thus obtained is subjected to analysis according to a conventional manner. The method of the invention is effective for the analysis of plural items using dry analytical elements.

According to the method of the invention, plasma separation from whole blood can be achieved efficiently, and recovered volume of plasma can be increased. By selecting reagent, good plasma which has no deviation in component viewpoint, and which is possible to measure in the same level accuracy as a plasma obtained by centrifuging, can be obtained through a simple filtration operation.

EXAMPLES

Example 1

① Assembling of Filter Unit

Figure 1:
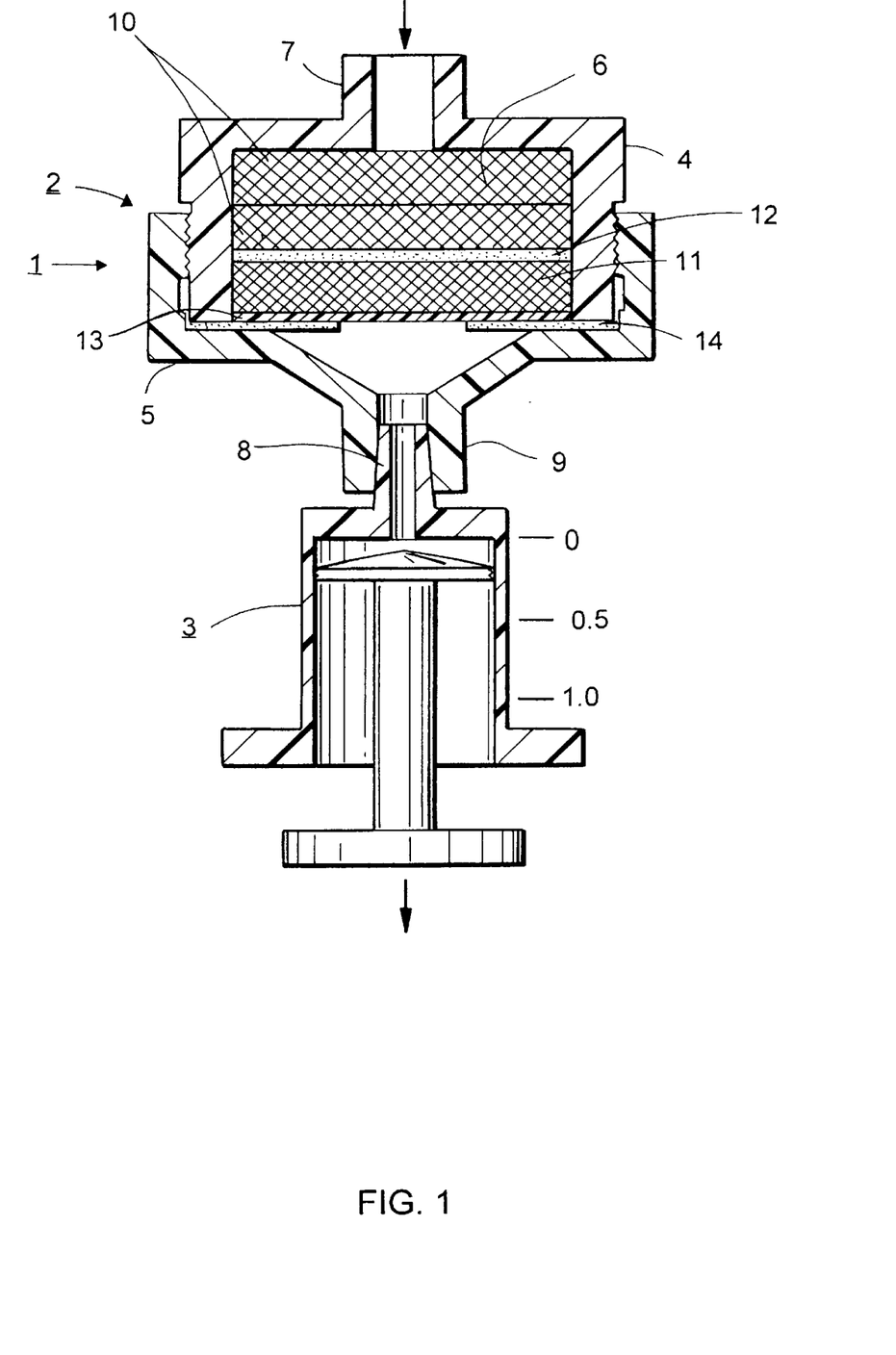
FIG. 1 is a sectional view of a filter unit used in Examples.
Figure 2A:
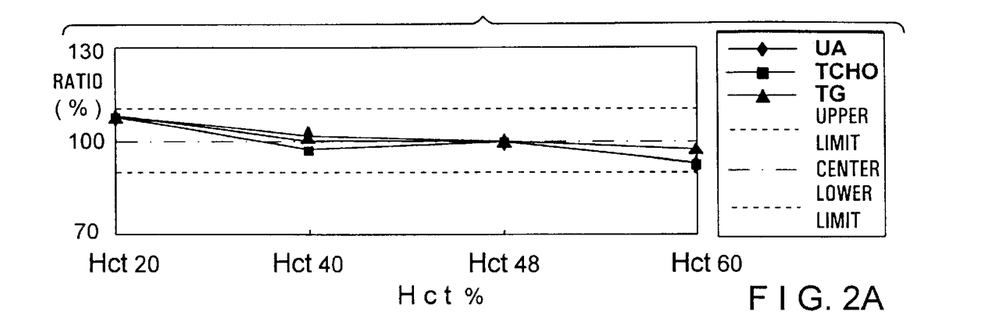
FIG. 2 shows graphs indicating variation of various analytical values of plasmas obtained from whole bloods different in hematocrit value.
Figure 2B:
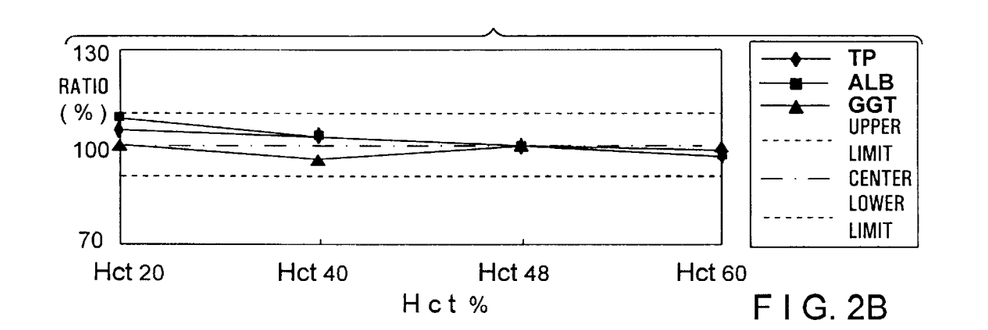
Figure 2C:
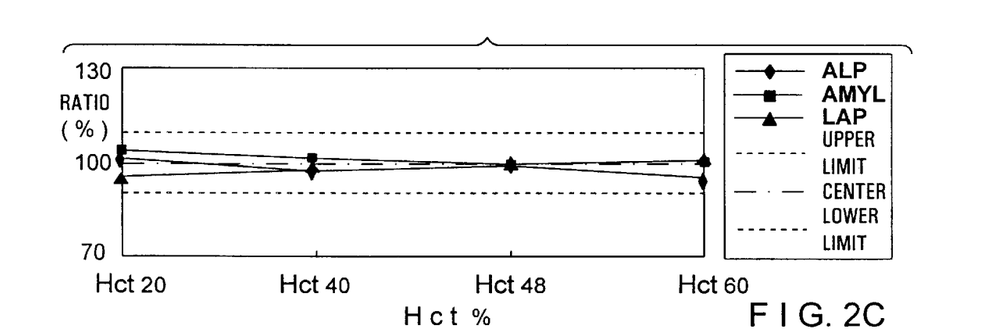
Figure 2D:
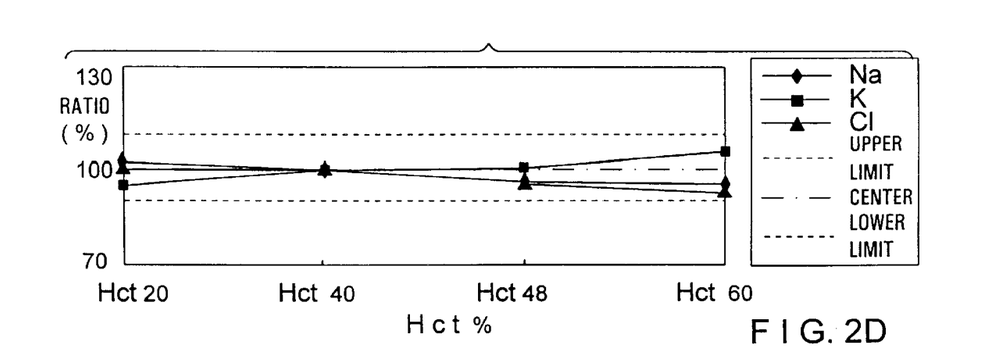

A filter unit shown in FIG. 1 was used. The filter unit 1 was composed of a filter holder 2 and a syringe 3. The fitter holder 2 was in a shape of short cylinder having a size of an outer diameter of 25 mm ø, an inner diameter of 20 mm ø, and was composed of a holder body 4 which contains filter material and a cap 5 which was screwed on the holder body 4. The lower end of the holder body was opened, and a filter chamber b was formed on the inside. A screw groove for screwing the cap 5 was formed on the lower part of outer peripheral wall of the holder body 4. On the other hand, the top of the holder body 4 was closed, and a sample intake 7 was projected toward outside at the center of the top. A screw groove which is screwed with the screw groove of the holder body 4 was formed at the upper part of the internal peripheral wall of the cap 5. The central part of the bottom of the cap 5 was inflated downward, and a suction part 9 which is fitted with a nozzle 8 of syringe 3 was projected.

The above filter holder 2 was turned, and superposed 2 sheets of glass fiber filter 10 (Whatman GF/D) punched into disc having a diameter of 20.1 mm θ were put in the filter chamber 6. The glass fiber filter 10 had an areal weight of 122.4 g/m², a thickness of 1.3 mm and a density of 0.094 g/cm³. A cellulose filter ("Cytosep", made by Cytosep) 11 having a thickness of 1 mm and a diameter of 20. 1 mm ø was fixed thereon by using a double face adhesive tape 12 having a diameter of 20.1 mm ø provided with an opening 13 mm ø in diameter. A polysulfone microporoces membrane ("PS", Fuji Photo Film Co, Ltd.) 13 having a pore size of 2 μm, a thickness of 0.15 mm and a diameter of 20.1 mm ø was superposed thereon, and an adhesive vinyl tape 14 having a diameter of 20.1 mmø provided with an opening 8 mmø diameter at the center was superposed further thereon and pressed to join it.

② Blood-Drawing 5 ml of whole blood was drawn from a healthy man with heparin. Hematocrit value of the blood was measured and found to be 44%.

③ Preparation of HL Agent

Lithium sulfate monohydrate ($Li_2So_4 \cdot H_2O$) was weighed, and dissolved in distilled water to obtain a 2 mol/l aqueous lithium sulfate solution.

④ Preparation of HL Agent-Added

Whole Blood with 30 μl of the HL agent solution prepared in ③ was pipetted into a 2 ml sample tube, and 1.5 ml of the whole blood with heparin was added thereto. Hematocrit value was measured and found to be 30%.

⑤ Filtration of Blood

The whole blood prepared in ④ was introduced into the filter unit assembled in ①, and sucked at a suction speed of 600 μg/min for 20 seconds. As a result, plasma was separated and accumulated on the polysulfone membrane in the inflated portion of the cap.

⑥ Recovery of Separated Plasma

Using a micropipette, separated plasma was taken out, and the volume of the plasma was measured. The volume was about 395 μl. Hemolysis did not occur. LDH activity of the plasma was measured and found to be 179 U/l. Since LDH activity of a control plasma separated by centrifusing without HL agent was 173 U/1, the LDH activity of the plasma obtained by the method of the invention was almost in the same level as the control plasma.

Since the volume of the glass fiber filters was 628 mm³, the half was 314 mm³ (i.e. 314 μl). By this example, it was confirmed that plasma in an amount of ½ or more of the volume of glass fiber filter(s) can be recovered easily and surely.

Comparative Example 1

① Preparation of $Li_2SO_4$-Impregnated Glass Fiber Filter Sheet 10 ml of 1 mol/l azueous $Li_2SO_4$ solution was prepared, and placed in a Petri dish 50 mm ø in diameter, glass fiber filters (Whatman GF/D) punched into disc 20 mm ø in diameter were immersed in the aqueous $Li_2SO_4$ solution to be impregnated with about 1 ml/cm², and allowed to stand at room temperature followed by drying at 60° C. for 3 hours.

② Assembling of Filter Unit

Two sheets of the $Li_2SO_4$-impregnated glass fiber filter prepared in ① was put in the filter chamber 6, and a filter unit was prepared similar to Example 1.

③ Preparation of Whole Blood 5 ml of whole blood was drawn from a healthy man with heparin, and 1.5 ml of the whole blood was put in a sample tube.

④ Filtration of Blood

Using the filter unit assembled in ②, the whole blood was filtered with suction similar to Example 1. As a result, about 230 μl of plasma was obtained, but the plasma was made red by hemolysis. Hb concentration of the plasma was in a level corresponding to 150 to 200 mg/dl. LDH activity of the plasma was measured and found to be 350 IU/l. On the other hand, the LDH activity of the whole blood to which $Li_2SO_4$ was not added was 192 IU/l.

Comparative Example 2

Instead of 2 mol/l aqueous $Li_2SO_4$ solution in Example 1, saline was add to the whole blood, and lowering degree of hematocrit (Hct) was examined, to 1.5 ml of the whole blood with heparin, saline was added, and after mixing, hematocrit value was measured. Two levels of the whole blood of healthy person (Hct 44%) and a high hematocrit whole blood (Hct 54%) were examined.

The results are summarized in table 1. In the case of using saline, since contraction of erythrocyte did not occur, the lowered degree of hematocrit value was almost consistent with the calculated based on mere dilution.

It was confirmed that Hct lowering does not occur in the above concentrations.

TABLE 1

| Whole Blood Hct (%) | Amount of Saline (μl) | Hct after Dilution (%) Measured Value | Calculated Value |
|---|---|---|---|
| 41 | 75 | 39 | 39 |
|  | 150 | 38 | 37 |
|  | 300 | 34 | 34 |
|  | 1500 | 21 | 21 |
| 57 | 75 | 55 | 54 |
|  | 150 | 52 | 52 |
|  | 300 | 48 | 48 |
|  | 1500 | 28 | 29 |

Example 2

Blood was drawn from healthy women to obtain 20 ml whole blood with. Hematocrit value of the blood was measured and found to be 41%. A part of the blood was centrifuged to separate plasma to prepare high hematocrit whole blood samples. The plasma was added to the original whole blood to prepare a low hematocrit whole blood. Thus, 5 types (No.1–No.5) of whole blood samples different in hematocrit value were prepared.

To each No.1–No.5samples, 2 mol/l $Li_2SO_4$ was added in an amount of 50 μl per 1 ml whole blood. The sample was filtered with suction using the same filter unit as Example 1, provided that the whole blood sample was introduced from the upside, and a 5 ml syringe was fitted into the suction port located on the underside. Suction was carried out, in a displacement of 800 μl for 30 seconds. The volume of the glass fiber filter was 185 mm² (i.e. 185 μl). Recovered volumes of each sample are summarized in Table 2.

TABLE 2

| Hct (%) |  | 20 | 41 | 48 | 59 | 68 |
|---|---|---|---|---|---|---|
| Recovered Plasma Volume (μl) | Inventive Example 2 | 540 | 410 | 325 | 215 | 180 |
|  | Comparative Example 3 | 200 | 130 | 80 | 35 | 10 |

Comparative Example 3

Using the same filter unit, the same whole blood samples were filtered without adding $Li_2SO_4$. The results are also shown in Table 2. The higher the hematocrit value of the whole blood was, the greater the effect of the HL agent was, In the case of the hematocrit value of 48% or less, the recovered plasma was about ¼ to ½.₇ of that of using HL agent, but in the case of 59%, the ratio was ⅐.

In the case of 68%, the amount of recovered plasma was very small. In the case of the hematocrit value of 48% or more, hemolysis was observed more or less.

Example 3

In an experiment similar to Example 1, 15 μl aqueous 2 mol/l $Li_2SO_4$ solution was added to 1.5 ml whole blood, and the blood was filtered similar to Example 1. As a result, 228 μl of plasma was recovered without hemolysis The Hct value was 48% before adding HL agent and 42% after adding it.

Components of the plasma thus recovered were measured by using two analyzers ("Fuji Drichem 5500", "Fuji Drichem 800", Fuji Photo Film Co., Ltd.). Using a calibration curve which had been prepared using the plasma obtained by centrifuging the whole blood to which $Li_2SO_4$ was added in the same concentration, concentration of each component was determined from the measured result. The results are summarized in Table 3. As a control, components of the plasma obtained by centrifuging the whole blood without adding the HL agent were measured. It was confirmed that all 23 analytical items can be measured in the same level of accuracy as the control

TABLE 3

| No. | Item | Unit | Measured Value CONTROL | SAMPLE | % |
|---|---|---|---|---|---|
| 1 | GLU | mg/dl | 107 | 106 | 99 |
| 2 | BUN | mg/dl | 16.6 | 17 | 102 |
| 3 | CRE | mg/dl | 0.9 | 0.9 | 100 |
| 4 | UA | mg/dl | 6.2 | 6.2 | 100 |
| 5 | TCHO | mg/dl | 171 | 174 | 102 |
| 6 | TG | mg/dl | 65 | 64 | 99 |

TABLE 3-continued

| No. | Item | Unit | Measured Value CONTROL | SAMPLE | % |
|---|---|---|---|---|---|
| 7 | TBIL | mg/dl | 0.8 | 0.9 | 113 |
| 8 | Ca | mg/dl | 9.4 | 9.7 | 103 |
| 9 | IP | mg/dl | 2.3 | 2.2 | 96 |
| 10 | TP | g/dl | 7.9 | 7.7 | 98 |
| 11 | ALB | g/dl | 4.8 | 4.8 | 100 |
| 12 | GGT | U/I | 20 | 19 | 95 |
| 13 | GOT | U/I | 14 | 16 | 114 |
| 14 | GPT | U/I | 12 | 13 | 108 |
| 15 | CPK | U/I | 125 | 127 | 102 |
| 16 | LDH | U/I | 152 | 160 | 105 |
| 17 | ALP | U/I | 225 | 224 | 100 |
| 18 | AMYL | U/I | 67 | 67 | 100 |
| 19 | LAP | U/I | 58 | 61 | 105 |
| 20 | NH$_3$ | mg/dl | 39 | 41 | 105 |
| 21 | Na | mep/l | 138 | 137 | 99 |
| 22 | K | mep/l | 3.6 | 3.6 | 100 |
| 23 | Cl | mep/l | 99 | 98 | 99 |

The whole blood was also filtered without HL agent, and in this case, plasma without hemolysis was not recovered Example 4

A whole blood was separated into blood cells and plasma, and then both were mixed at a different ratio to prepare whole blood samples having a hematocrit value of 20%, 40%, 48% and 60%. The samples were treated similar to Example 3, and measured by using an analyzer "Hitachi 7150" and an electrolyte analyzer "Fuji Drichem 800".

The results are shown in FIG. 2. As shown in FIG. 2, as to all analytical items, deviation of the measured results from control was within the range of ±10% over all hematocrit value range of 20 to 60%. Moreover, the deviation on the basis of the measured value at Hct 48% was within±5% except only a part of items.

Example 5

In an experiment similar to Example 1, $Cs_2SO_4$ was used as the HL agent instead of $Li_2SO_4$. 60 μl of 2 mol/l $Cs_2SO_4$ aqueous solution was added to 1.5 ml whole blood with heparin. The Hct value was 38% before adding the HL agent and 31% after the addition thereof.

The whole blood containing the HL agent was filtered with suction similar to Example 1, and 320 μl plasma without hemolysis was obtained.

Components of the plasma were measured by an analyzer ("Fuji Drichem 3000", Fuji Photo Film Co., Ltd.)

In comparison, the above whole blood before adding the HL agent was centrifuged to obtain plasma, and components of the plasma were also measured. The results are summarized in Table 4.

TABLE 4

| | | | CONTROL | Sample | | |
|---|---|---|---|---|---|---|
| No | Item | Correction Factor | Measured Value | Measured Value | Corrected Value | Judgement |
| 1 | GLU | 0.95 | 92.00 | 80.00 | 84.21 | Δ |
| 2 | BUN | 0.95 | 15.80 | 15.00 | 15.79 | ⊙ |
| 3 | CREA | 0.90 | 0.90 | 0.80 | 0.89 | ⊙ |
| 4 | UA | 0.85 | 4.70 | 4.00 | 4.71 | ⊙ |
| 5 | TCHO | 0.85 | 191.00 | 161.00 | 189.41 | ⊙ |
| 6 | TG | 0.90 | 58.00 | 55.00 | 61.11 | ○ |
| 7 | TBIL | 0.90 | 1.10 | 1.00 | 1.11 | ⊙ |
| 8 | Ca | 1.00 | 9.90 | 10.10 | 10.10 | ○ |
| 9 | IP | 0.90 | 2.60 | 2.30 | 2.56 | ⊙ |
| 10 | TP | 0.90 | 7.50 | 6.90 | 7.67 | ○ |
| 11 | ALB | 0.60 | 4.50 | 2.60 | 4.38 | ○ |
| 12 | GGT | 0.85 | 17.00 | 14.00 | 16.47 | ⊙ |
| 13 | GOT | 0.85 | 18.00 | 15.00 | 17.65 | ⊙ |
| 14 | GPT | 0.85 | 17.00 | 15.00 | 17.65 | ⊙ |
| 15 | CPK | 0.85 | 96.00 | 83.00 | 97.65 | ⊙ |
| 16 | LDH | 0.90 | 148.00 | 135.00 | 150.00 | ⊙ |
| 17 | ALP | 0.85 | 87.00 | 79.00 | 92.94 | ⊙ |
| 18 | AMYL | 0.50 | 83.00 | 41.00 | 82.00 | ⊙ |
| 19 | LAP | 0.80 | 41.00 | 34.00 | 42.50 | ⊙ |
| 20 | NH$_3$ | 1.00 | 77.00 | 147.00 | 147.00 | x |
| 21 | Na | 1.00 | 138.00 | 137.00 | 137.00 | ⊙ |
| 22 | K | 1.00 | 4.20 | 4.00 | 4.00 | ⊙ |
| 23 | Cl | 0.95 | 100.00 | 94.00 | 98.95 | ⊙ |
| 24 | HDLC | 0.85 | 69.00 | 62.00 | 72.94 | Δ |

In the above table, the decrease of the measured values are seemed to depend on the dilution by the water discharged from blood cells to plasma caused by the addition of the EL agent. Accordingly, the measure value of each component was corrected by the correction factor in Table 4 and the corrected values were also indicated. The judgement was made based on the allowance in clinical assay, as follows; ⊙:Very excellent, ○:Excellent, Δ:Good, x: Failure.

Example 6

Seven HL agents which brought good results with respect to the measurement of electrolytes, expecially Na, K, Cl and Ca which are important in clinical assay, were selected.

Similar experiments to Example 1 were carried out using the HL agents, and influences upon measured values of Na, K and Cl were examined. The results are summarized in Table 5.

Table 5

TABLE 5

| HL Agent | HL Effects | Less Hemolysis | PFT Ability | Electrolyte | | |
|---|---|---|---|---|---|---|
| | | | | Na | K | Cl |
| Asp.Na | ⊚ | ○ | ○ | x | ○ | ○ |
| CaCl$_2$ | ⊚ | ○ | ○ | ○ | ○ | x |
| NaCl | ⊚ | ○ | ○ | x | ○ | x |
| LiNO$_3$ | ⊚ | ○ | ○ | ○ | ○ | x |
| Li$_2$SO$_4$ | ⊚ | ○ | ○ | ○ | ○ | ○ |
| Rb$_2$SO$_4$ | ⊚ | ○ | ○ | ○ | x | ○ |
| Cs$_2$SO$_4$ | ⊚ | ○ | ○ | ○ | ○ | ○ |

As shown in Table 5, Li$_2$SO, and Cs$_2$SO$_4$ were especially excellent as HL agent. In Table 5, HL agents containing the same ion species as the target analyte are unsuitable.

For example, since Asp, Na containing Na species, it is unsuitable for measuring Na. Even when an HL agent does not contain the same ion species as the target analyte, the HL agent containing an analogous ion which interferes with the measurement of the target analyte by an ion-selective electrode, is also unsuitable. Accordingly, in Table 5, the HL agents which are indicated by X can be used by substituting an ion species suitable for the measurement for the same or analogous ion species in each HL agent. All of the HL agents in Table 5 are usable as the HL agent, unless measuring electrolyte.

We claim:

1. A method of preparing a plasma or serum sample from whole blood which comprises mixing an aqueous solution of an inorganic salt or an amino acid or salt thereof having a concentration of 0.1 to 5 mol/l with the whole blood in an amount of 20% or less of the whole blood volume so that amount of said inorganic salt or said amino acid or salt thereof becomes 10 to 200 μmol/ml of whole blood, and then, filtering the whole blood to remove blood cell components, wherein said inorganic salt is a combination of monovalent or divalent alkali metal or alkaline earth metal and a member selected from the group consisting of halogen, NO$_3$, SO$_4$, and CO$_3$, and wherein filtering material used in said filtering comprises glass fiber filter having a density of 0.02 to 0.3 g/cm$^3$.

2. The method of claim 1 wherein said filtering material further comprises a microporous membrane.

3. The method of claim 2 wherein said microporous membrane is a fluorine-containing polymer membrane or polysulfone membrane.

4. The method of claim 1 wherein said filtering is carried out without agglutination.

5. The method of claim 1, wherein said whole blood has a hematocrit value of 50 to 70%.

6. A method of preparing a plasma or serum sample from whole blood consisting essentially of mixing an aqueous solution of an inorganic salt or an amino acid or salt thereof having a concentration of 0.1 to 5 mol/l with the whole blood in an amount of 20% or less of the whole blood volume so that amount of said inorganic salt or said amino acid or salt thereof becomes 10 to 200 μmol/ml of whole blood, and then, filtering the whole blood to remove blood cell components, wherein said inorganic salt is a combination of monovalent or divalent alkali metal or alkaline earth metal and a member selected from the group consisting of halogen, NO$_3$, SO$_4$, and CO$_3$, and wherein filtering material used in said filtering comprises glass fiber filter having a density of 0.02 to 0.3 g/cm$^3$.

* * * * *